United States Patent [19]

Fischer

[11] 4,187,161
[45] Feb. 5, 1980

[54] ELECTRICAL ELEMENT OF CONSTRUCTION

[75] Inventor: Wulf Fischer, Iserlohn, Fed. Rep. of Germany

[73] Assignee: Garching Instrumente, Munich, Fed. Rep. of Germany

[21] Appl. No.: 941,435

[22] Filed: Sep. 11, 1978

[30] Foreign Application Priority Data

Feb. 15, 1978 [DE] Fed. Rep. of Germany ....... 2806464

[51] Int. Cl.² ..................... G01N 27/58; H01M 8/10; H01M 8/12; H01L 29/66
[52] U.S. Cl. ................................. 204/195 S; 357/7; 357/25; 357/61; 361/433; 361/434; 361/435; 429/191
[58] Field of Search ............... 361/433, 434, 435, 436; 357/10, 7, 25, 61; 429/191; 204/195 S, 1 S

[56] References Cited

U.S. PATENT DOCUMENTS 3,310,443  3/1967  Fessler et al. ..................... 357/29 X

OTHER PUBLICATIONS

G. Holzäpfel et al., Festkörperprobleme, XV, pp. 317–349, (1975).
Jack H. Elliott, Nuclear Instruments and Methods, vol. 12, pp. 60–66, (1961).

Primary Examiner—G. L. Kaplan
Attorney, Agent, or Firm—Sprung, Felfe, Horn, Lynch & Kramer

[57] ABSTRACT

An electrical element which comprises at least one circuit component consisting of a solid ionic conductor, and wherein the electron flow through the ionic conductor is supressed without substantially hindering the ion flow therethrough, by at least one pn junction formed across the direction of ion flow. The pn junction is formed by at least one of p-conductive and n-conductive zones in or adjoining the ionic conductor and which is capable of being reversed-biased relative to the electron flow. The p-conductive and n-conductive zones comprise a material conductive of the same ions as the ionic conductor.

12 Claims, 3 Drawing Figures

ELECTRICAL ELEMENT OF CONSTRUCTION

BACKGROUND

The invention relates to an electrical element of construction having at least one circuit component consisting of a solid ionic conductor, especially in ionically conductive solid electrolyte.

Said ionic conductors and ionically conductive solid electrolytes carry the electrical current substantially by means of ions. In addition to the ionic transport associated with a mass transport corresponding to Faraday's Law, however, electronic currents also flow in the solid ionic conductors and solid electrolytes. The contribution of ionic conduction and of electronic conduction to the total conductivity of the substance is characterized by the transference number, which is the ratio of the partial conductivity of the kinds of particles involved in the conduction of current to the total conductivity. In the case of solid, mixed ionic conductors, the transference number of the ionic conduction is substantially greater than the transference number of the electronic conduction.

Solid electrolytes are used as substitutes for liquid electrolytes in electrochemical energy storage and as electrolytes in galvanic measuring cells for the determination of thermodynamic and kinetic information on chemical reactions (G. Holzäpfel and H. Rickert, "High Ionic Conductivity in Solids—Theoretical Aspects and Application," *Festkörperprobleme* XV, 1975, pp. 317 to 349, Verlag Pergamon, Vieweg, and A. F. Bogenschütz, W. Krusemark, "Elektrochemische Bauelemente," pp. 18, 19 and 41 to 46, 1976, Verlag Chemie, Weinheim). The surface of the ionic conductor and of the solid electrolyte is commonly contacted by two electronically conductive electrodes spaced apart from one another, one of which ionizes the corresponding atoms or molecules and yields the ions to the ionic conductor or solid electrolyte, and the other discharges the ions. While the ions migrate through the ionic conductor or solid electrolyte, as the case may be, the electron transport is accomplished through a circuit between the electrodes. The atoms or molecules to be ionized can originate, for example, from the material substance of the electrodes, as is the case, for example, in electrochemical energy storage (batteries), but they can also be supplied from without through porous electrodes, as is the case, for example, in measuring probes.

In most applications, the ionic conductivity is to be as great as possible, while the electronic conductivity is to be negligible. Although a series of solid ionic conductors and solid electrolytes has become known, the above conditions are more or less well fulfilled by only a few substances. In particular, the number of solid electrolytes having technically practical properties is still very small. Examples of technically practical solid electrolytes are AgI, RbAg$_4$I$_5$, β-aluminum oxide (β-Na$_2$O.11Al$_2$O$_3$), doped ZrO$_2$ and CaF$_2$. On the other hand, a large number of mixed ionic conductors have become known which have very limited usefulness on account of the high transference number of the electronic conduction.

THE INVENTION

The object of the invention is to find a method whereby the transference number of the electronic conduction can be made negligibly small in solid ionic conductors and especially ionically conductive solid electrolytes.

This object is achieved by the fact that, for the suppression of the electron flow through the ionic conductor or solid electrolyte, as the case may be, at least one pn junction which can be reverse-biased is formed across the direction of ionic flow, and its p-conducting or n-conducting zone consists in each case of a material conducting the ions of the ionic conductor or solid electrolyte, as the case may be.

The reverse-biased pn junction suppresses the electron flow through the ionic conductor or solid electrolyte, but substantially does not hinder the ion flow. Problems which arise out of the electronic conduction of the ionic conductors or solid electrolytes can thus be disregarded, so that the number of practical ionic conductors and solid electrolytes is considerably increased. The technically usable ionic conductors and solid electrolytes can be selected for optimum characteristics especially also with regard to their corrosion performance and their reactivity with substances of their environment, especially the substances of the electrodes.

The pn junction can be formed by making the ionic conductor or solid electrolyte to consist of a p-conductive or n-conductive material, and having the ionic conductor or solid electrolyte adjoined by a zone of material consisting of an ionic conductor or solid electrolyte of the opposite type of conductivity, conducting the same ions. These can be ionic conductors or solid electrolytes which of their very nature have different types of conductivity. The different types of conductivity, however, can also be brought about by doping adjoining zones with acceptors or donors, as the case may be.

Depending on the embodiment, the n-conductive and the p-conductive zone of the pn junction could be provided with terminals to which an external voltage source is connected. Preferred, however, are embodiments in which the zones of opposite conductivity of the pn junction are so disposed with respect to the electromotive force (emf) of the circuit component, as determined by the direction of ion flow through the ionic conductor or solid electrolyte, that the pn junction is reverse-biased by the emf.

To be able to operate the element of construction in a bipolar manner, a pnp junction or an npn junction can be formed across the direction of ion flow in or adjoining the ionic conductor or solid electrolyte. Such junctions can, like the unipolar pn junction, be formed by doping the ionic conductor or solid electrolyte with donors or acceptors or they can be formed as a series circuit of mixed ionic conductors or solid electrolytes of opposite types of conductivity.

The middle zone of the pnp or npn junction of such construction elements can be contacted by a control electrode which in turn can be connected to a circuit supplying a blocking voltage. Such circuits are known, for example, from transistor technology for the establishment of the base bias. Furthermore, a circuit can be used to control the electron current through the ionic conductor or solid electrolyte.

The ionic conductor or solid electrolyte is disposed between two electrodes, one of which consists of a material which yields the ions or is physically permeable for the ions or the substances containing them, and the other electrode consists of a material receiving the ions or permeable to the ions. Preferably, one or both electrodes are formed by the ionic conductor or solid electrode and/or the material of the pn junction.

The invention is used preferably in energy cells or measuring probes which are known in themselves. In energy cells it makes possible the optimation of the solid electrolyte with regard to energy density and power density, and with regard to mechanical stability and resistance to corrosion. Furthermore, it permits the selection of solid electrolytes which achieve electrochemical reactions of sufficient magnitude even at low temperatures. When the invention is embodied in a measuring probe, a series of otherwise hard-to-measure thermodynamic magnitudes can be determined, such as chemical potential, activity, or energy of formation. Entropies and enthalpies can be computed on the basis of the temperature-dependence of the emf of a galvanic cell. Another field of application is in measuring probes for the direct electrical measurement and control of kinetic processes in chemical reactions, condensation and evaporation processes, diffusion processes in solids, liquids or gases, phase boundary processes, and the like.

DESCRIPTION OF THE DRAWINGS

The invention will be explained below with the aid of the drawing wherein.

DESCRIPTION OF THE INVENTION

Figure 1:
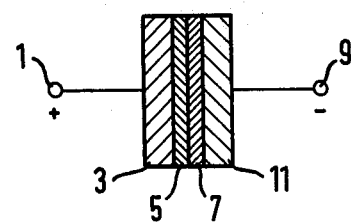
FIG. 1 is a diagrammatic representation of an energy cell having a pn junction.

FIG. 1 shows the construction of an energy cell consisting of a first electrode 3 provided with a terminal 1, an adjoining layer 5 of a p-conductive or n-conductive solid electrolyte material, a layer 7 adjoining layer 5 and composed of a solid electrolyte material of the opposite type of conductivity, and a second electrode 11 adjoining the layer 7 and provided with a terminal 9. The solid electrolyte material of layers 5 and 7 conducts the same type of ion. The electrode 3 consists of a material that can be ionized to ions of this type. The material of electrode 11 is selected such that it can discharge and absorb these ions. The materials of electrodes 3 and 11 have different positions within the electrochemical voltage series and, unless they are metals, they are made electronically conductive by the addition of metal or carbon.

The types of conductivity of layers 5 and 7 are selected such that the emf of the energy cell reverse-biases the pn junction formed by the layers 5 and 7, so that the electronic current is blocked by layers 5 and 7, preventing an internal discharge of the energy cell. If, for example, the electrode 11 yields negatively charged ions, the layer 7 consists of an n-conducting solid electrolyte material.

In an energy cell that was tested in practice, the positive electrode 3 consisted of silver, layer 5 of $Ag_2Te$ (p-conductive), layer 7 of $Ag_2S$ (n-conductive) and the negative electrode 11 of sulfur, to which carbon had been added for the improvement of conductivity. Measurements showed that the electronic conductivity at room temperature is lowered by a factor of $10^2$ by the influence of the pn junction when biased by a reverse voltage of 236 mV. The ionic conduction is not affected by the pn junction.

Figure 2:
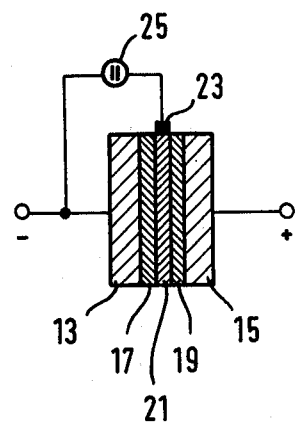
FIG. 2 is a diagrammatic representation of an energy cell having an npn or pnp junction.

FIG. 2 shows an embodiment in which, unlike the embodiment in FIG. 1, two layers 17 and 19 of an n-conductive solid electrolyte material are disposed between a first electrode 13 and a second electrode 15 of an energy cell. Between the layers 17 and 19 there is placed a layer 21 of a p-conducting solid electrolyte material. The layers 17 to 21 are again permeable to the ions given off by one of the two electrodes 13 or 15 or absorbed by the other electrode. The layer 21 is contacted by a control electrode 23, to which there is connected a voltage source 25 for the production of a reverse voltage, as is known from the transistor art. The layers 17 and 19 can consist of the same solid electrolyte material.

Figure 3:
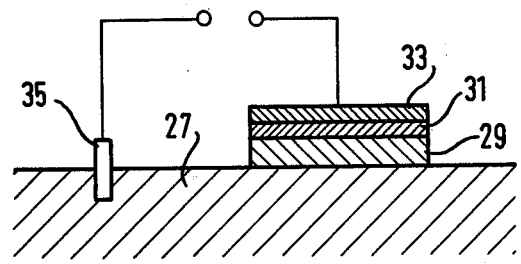
FIG. 3 is a diagrammatic representation of the measuring probe for the measurement of the oxygen content of a molten substance.

FIG. 3 shows the construction of a measuring probe by which the oxygen content of a molten metal 27 can be measured. A body 29 of a solid electrolyte material of a first type of conductivity is placed on the surface of or immersed in a molten metal 27. Across the direction of ion flow of body 29 is a layer 31 of an oxygen ion conducting solid electrolyte material of the opposite type of conductivity, which is covered with a porous layer 33 of platinum which is permeable to oxygen. Beside the body 29 an inactive electrode 35 is immersed in the molten metal 27. The partial pressure gradient between the oxygen dissolved in the molten metal 27 and the atmospheric oxygen drives the oxygen ions through the solid electrolyte of body 29 and layer 31, a voltage (emf) forming between the electrode 35 and the platinum layer 33, which is a measure of the oxygen content of the molten metal 27. The type of conductivity of body 29 and of layer 31 is selected such that the pn junction formed between them is reverse-biased. Erroneous measurements on the basis of the electron currents between the molten metal and the platinum layer 33 are prevented.

In the embodiments shown in FIGS. 1 to 3, the solid electrolytes are represented in layer form. Other embodiments are conceivable, depending on the requirements. The layers can consist of different solid electrolyte materials; however, layers consisting of one and the same solid electrolyte material doped with suitable donors or acceptors for the formation of the pn junction or junctions are also suitable.

It will be understood that the specification and examples are illustrative but not limitative of the present invention and that other embodiments within the spirit and scope of the invention will suggest themselves to those skilled in the art.

What is claimed is:

1. An electrical component having a circuit comprising between at least two points thereof, a solid ionic conductor so that the current between the two points is substantially an ionic current and means for suppressing the electron flow through the ionic conductor without substantially hindering the ion flow therethrough including at least one pn junction formed across the direction of ion flow in or adjoining the ionic conductor and which is capable of being reversed biased relative to the electron flow and wherein the p-conductive and n-conductive zones of the p-n junction comprise material conductive of the same ions as the ionic conductor.

2. The component as claimed in claim 1 wherein the ionic conductor comprises one of a p-conductive or n-conductive material and is adjoined by a zone of solid ionic conductor material conductive of the same ions and of the opposite type of conductivity.

3. The component as claimed in claim 1 wherein the ionic conductor contains adjacent zones of which one is doped with acceptors and the other with donors to form the pn junction.

4. The component as claimed in claim 1 comprising zones of both types of conductivity forming the pn junction disposed with respect to the emf of the circuit component determined by the direction of the ion flow through the ionic conductor, such that the pn junction is reverse-biased by the emf.

5. The component as claimed in claim 1 wherein the means includes one of a pnp junction or an npn junction formed across the ion flow direction in or adjoining the ion conductor.

6. The component as claimed in claim 5 further comprising three zones of alternating conductivity and a control electrode contacting the middle zone of the pnp or npn junction.

7. The component as claimed in claim 6 further comprising circuitry connected to the control electrode for providing a reverse bias voltage.

8. The component as claimed in claim 1 further comprising two electrodes between which the ionic conductor is disposed and wherein one electrode consists of a material which is one of yielding of the ions or physically permeable to the ions or the substances containing them and the other electrode consists of a material which is correspondingly absorbing of the ions or permeable to the ions.

9. The component as claimed in claim 8 wherein at least one of the electrodes is formed by one of the ionic conductor or the material of the pn junction.

10. The component as claimed in claim 1 wherein the solid ionic conductor comprises an ionically conductive solid electrolyte.

11. An energy cell comprising the component according to claim 1.

12. A measuring probe for the conversion of chemical characteristics which determine ion current to electrical signals comprising the component according to claim 1.

* * * * *